(12) United States Patent
Lohray et al.

(10) Patent No.: US 8,030,345 B2
(45) Date of Patent: Oct. 4, 2011

(54) TRICYCLIC PYRAZOLE DERIVATIVES AS CANNABINOID RECEPTOR MODULATORS

(75) Inventors: Braj Bhushan Lohray, Gujarat (IN); Vidya Bhushan Lohray, Gujarat (IN); Brijesh Srivastava, Gujarat (IN)

(73) Assignee: Cadila Healthcare Limited, Ahmedabad (IN)

( * ) Notice: Subject to any disclaimer, the term of this patent is extended or adjusted under 35 U.S.C. 154(b) by 1033 days.

(21) Appl. No.: 11/632,236

(22) PCT Filed: Jul. 8, 2005

(86) PCT No.: PCT/IN2005/000237
§ 371 (c)(1),
(2), (4) Date: Aug. 24, 2007

(87) PCT Pub. No.: WO2006/025069
PCT Pub. Date: Mar. 9, 2006

(65) Prior Publication Data
US 2008/0051386 A1    Feb. 28, 2008

(30) Foreign Application Priority Data
Jul. 12, 2004    (IN) .......................... 745/MUM/2004

(51) Int. Cl.
*A61K 31/38*   (2006.01)
*C07D 495/02*   (2006.01)
(52) U.S. Cl. ......................................... 514/431; 549/11
(58) Field of Classification Search .................. None
See application file for complete search history.

(56) References Cited

FOREIGN PATENT DOCUMENTS
WO    01/32629    5/2001
WO    01/32663    5/2001

OTHER PUBLICATIONS

Wermuth. The Practice of Medicinal Chemistry, 1996, pp. 203-237.*
Grant et al. Clinical Neuroscience Research, 2005, 5, 185-199.*
U.S. Appl. No. 12/769,861, filed Apr. 2010, Lohray.*
Stoit, A. R.,et al. "Design, Synthesis and Biological Activity of Rigid Cannabinoid $CB_1$ Receptor Antagonists." *Chem Pharm. Bull* (2002) vol. 50, No. 8, pp. 1109-1113.
Ruiu, S., et al. Synthesis and Characterization of NESS 0327: A Novel Putative Antagonist of the $CB_1$ Cannabinoid Receptor.: *The Journal of Pharmacology and Experimental Therapeutics* (2003) vol. 306, No. 1, pp. 363-370.
Fravolina, A., et al. "Synthesis and pharmacological activity of benzothiopyranopyrazole and benzothiopyranoisoxazole and benzothi opyranoisoxazole carboxamides." *FARMACO, Edizione Scientifica, Societa Chimica Italinana, Pavia, It.* (1978) vol. 33, No. 11, pp. 855-865.
Mussinu, J-M., et al. "Tricyclic Pyrazoles. Part 1: Synthesis and Biological Evaluation of Novel 1,4-Dihydroindeno[1,2-c]pyrazol-based Ligands for $CB_1$ and $CB_2$ Cannabinoid Receptors." *Bioorganic & Medicinal Chemistry* (2003) vol. 11, pp. 251-263.

* cited by examiner

*Primary Examiner* — Noble Jarrell
(74) *Attorney, Agent, or Firm* — Ladas & Parry LLP

(57) ABSTRACT

The present invention relates to novel compounds of general formula (I),

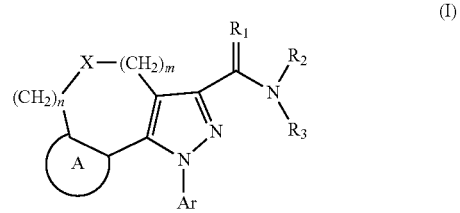

their regioisomers, tautomeric forms, novel intermediates involved in their synthesis. The present invention also relates to a process of preparing compounds of general formula (I), their regioisomers, their tautomeric forms, their pharmaceutically acceptable salts, pharmaceutical compositions containing them, and novel intermediates involved in their synthesis.

12 Claims, No Drawings

TRICYCLIC PYRAZOLE DERIVATIVES AS CANNABINOID RECEPTOR MODULATORS

FIELD OF INVENTION

The present invention relates to novel compounds of general formula (I), their regioisomers, tautomeric forms, novel intermediates involved in their synthesis, their pharmaceutically acceptable salts and pharmaceutical compositions containing them. The present invention also relates to a process of preparing compounds of general formula (I), their regioisomers, their tautomeric forms, their pharmaceutically acceptable salts, pharmaceutical compositions containing them, and novel intermediates involved in their synthesis.

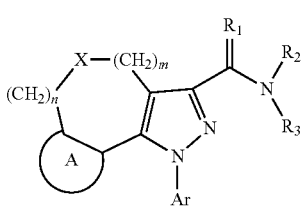

(I)

BACKGROUND AND PRIOR ART

Cannabinoids are present in Indian hemp *Cannabis sativa* and have been well known for their medicinal properties for ages. Cannabinoids as a therapeutic agents is however a recent phenomenon. (Williamson E. M. & Evans E. J. Drugs 2000 December; 60(6): 1303-14) Research in this area over the last decade have provided very important information on the cannabinoid receptors and their agonists and antagonists. Development of central Cannabinoid receptor ligands with lower lipophilicity.(*J. Med. Chem.* 2003; 46:642-645) Further cloning and isolation of two different subtypes of cannabinoid receptors—$CB_1$ (central subtype) and $CB_2$ (peripheral subtype) and the first endogenous ligand N-arachidonyl ethanolamine amide(AEA); anadamide (Matsuda L A et. al., *Nature* 1990; 346:561-4; Devane W A et. al. *J. Med. Chem.* 1992; 35:2065-9; Munro, S. et. al., *Nature* 1993, 365, 61-5) have stimulated research in this field. There has also been an increased interest among the different pharmaceutical companies in developing drugs for the treatment of diseases connected with disorders of the cannabinoid systems (Greenberg D. A., *Drugs News & Perspectives* 1999; 12: 458; Kulkarni S. K. & Ninan, *Indian Journal of Pharmacology* 2001; 33: 170-184; Piomelli D et. al., *Trends Pharmacol Sci.* 2000 June; 21(6): 218-24). Several compounds which are either $CB_1$ &/or $CB_2$ antagonists have been reported and are under various stages of development for e.g. SR-141716 A(Sanofi), CP-272871 (fizer), LY-320135 (Eli Lily), AM-630 (Alexis), SR-144528 (Sanofi) etc. Novel compounds which are selective CB1 and/or CB2 antagonists, their preparation and their use in medicine have also been reported in U.S. Pat. Nos. 5,925,768, 6,344,474, 6,028,084, 5,462,960, EP 0656354, U.S. Pat. Nos. 6,432,984, 6,509,367 B1, U.S. Pat. No. 5,624,941, EP1230222, EP 122952, FR 2816938, FR 2761266, FR 2800375, EP 0656354, EP 0576357, WO 03027076, WO 03026648, WO 03026647, WO 03020217, WO 0158450, WO 0185092, WO 0132663, WO 0132629 which are incorporated as references in their entirety. Synthesis and biological evaluation of novel 4,5-dihydro-1H-benzo [g] indazole-based ligands for cannabinoid receptors has been described in *Bioorg. Med. Chem.*, 2005, 13, 3309-3320.

Synthesis of tricyclic pyrazole derivative (NESS 0327) as CB1 antagonist has been disclosed in *J. Pharmacology & Experimental Therapeutics*, 2003, 306(1), 363-370. Synthesis and activity of tricyclic pyrazole ligands for CB1 & CB2 receptors have been disclosed in *Bioorg. Med. Chem.*, 2003, 11, 251-263.

Structure elucidation of novel ring constrained biaryl pyrazole CB1 cannabinoid receptor antagonist has been described in *Magn. Reson. Chem.* 2003, 41, 265-268.

Synthesis and biological activity of rigid cannabinoid CB1 cannabinoid receptor antagonists has been disclosed in *Chem. Pharm. Bull.* 2002, 50, 1109-1113.

Tricyclic benzopyrazole derivatives as cyclooxygenase-2 (COX-2) inhibitors have been disclosed in WO 9609304, which is also incorporated herein as reference.

Though research in the area of cannabinoids have been going on for more than a decade there are only few medicines available which modulate the cannabinoid receptors and fewer with minor side effects. Looking at the beneficial effects of cannabinoids, it would be highly desired to develop compounds, which modulate the cannabinoid receptors, having better or comparable absorption, metabolic stability, and exhibiting lesser toxicity.

SUMMARY OF INVENTION

The present invention describes novel compounds useful as modulators of cannabinoid receptors. The novel compounds are defined by the general formula (I) below:

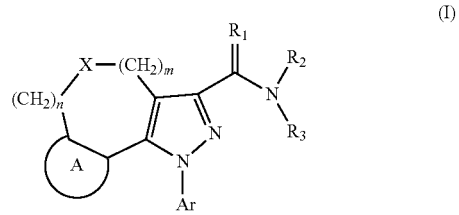

(I)

The compounds of the present invention mimic the actions of the cannabinoids making them useful for preventing or reversing the symptoms that can be treated with cannabis, some of its derivatives, and synthetic cannabinoids in a human or other mammalian subject. Preferably, the compounds of the present invention are selective antagonists of the cannabis $CB_1$-receptor.

PREFERRED EMBODIMENTS OF THE INVENTION

The object of the present invention thus is to provide novel compounds of general formula (I), their tautomeric forms, their regioisomers, novel intermediates involved in their synthesis, their pharmaceutically acceptable salts and pharmaceutical compositions containing them or their mixtures and their use in medicine.

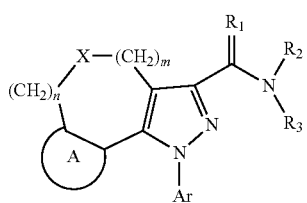

In an embodiment of the present invention is provided a process for the preparation of novel compounds of general formula (I), their regioisomers, their tautomeric forms, novel intermediates involved in their synthesis, pharmaceutically acceptable salts and pharmaceutical compositions containing them.

In another embodiment is provided pharmaceutical compositions containing compounds of general formula (I), their tautomeric forms, their regioisomers, their pharmaceutically acceptable salts and their mixtures having pharmaceutically acceptable carriers, solvents, diluents, excipients and other media normally employed in their manufacture.

In a further embodiment is provided a method of treatment of diseases which can be treated or whose symptoms can be reversed with cannabis or their derivatives both natural and synthetic, by administering a therapeutically effective & non-toxic amount of the compound of formula (I) or their pharmaceutically acceptable compositions to the mammals.

DETAILED DESCRIPTION

The novel compounds of the present invention are defined by the general formula (I) below:

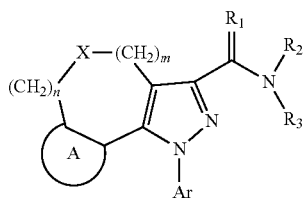

wherein 'Ar' represents single or fused groups selected from aryl, aralkyl, heterocyclyl, heteroaryl, heterocyclyl($C_1$-$C_2$) alkyl & heteroar($C_1$-$C_{12}$)alkyl group, each of them independently may optionally be substituted;

'A' represents optionally substituted heteroaromatic groups, "X" is selected from —$CH_2$—, O, S, SO, $SO_2$, or NR', where R' represents H, optionally substituted groups selected from linear or branched alkyl and cycloalkyl groups and, m & n represents integers such that $1 \leq m+n \leq 3$; or 'A' represents substituted aromatic group, "X" may be selected from O, S, SO, $SO_2$, or NR', where R' represents H, optionally substituted groups selected from linear or branched alkyl, and cycloalkyl groups and m & n represents integers such that $2 \leq m+n \leq 3$; or 'A' represents optionally substituted heterocyclic groups, "X" may be selected from —$CH_2$—, O, S, SO, $SO_2$, or NR', where R' represents H, optionally substituted groups selected from linear or branched alkyl and cycloalkyl groups and m & n represents integers such that $1 \leq m+n \leq 3$; or 'A' represents optionally substituted alicyclic groups, "X" may be selected from —$CH_2$—, O, S, SO, $SO_2$, or NR', where R' represents H, optionally substituted groups selected from linear or branched alkyl and cycloalkyl groups and m & n represents integers such that $1 \leq m+n \leq 3$; or $R_1$ represents O, S, or the group represented by N-Q, where Q represents H, substituted or unsubstituted groups selected from alkyl, aralkyl, aryl, heteroaryl or heterocyclic groups or the group represented by $SO_2R'$, where R' represents H, —OH, halogen or substituted or unsubstituted groups selected from alkyl, aralkyl, aryl, heteroaryl or heterocyclic or alicyclic groups;

$R_2$ is either H or ($C_1$-$C_6$) alkyl; $R_3$ is —$\overset{\oplus}{N}R_aR_bR_c$ or —$NR_bR_a$ where $R_a$ is ($C_1$-$C_6$)alkyl or $R_a$ forms a bridge containing 1-2 atoms, with one of the atoms of the heterocyclic radical formed by —$NR_bR_c$;

$R_b$ and $R_c$ represents optionally substituted groups selected from alkyl, aralkyl or alkenyl or $R_b$ & $R_c$ together with the nitrogen atom to which they are bonded, form a saturated or unsaturated heterocyclic or heteroaromatic radical which may be optionally substituted and may be fused;

The substituents on 'A' may be selected from hydroxyl, oxo, halo, thio, nitro, amino, cyano, formyl, optionally substituted groups selected from linear or branched alkyl, haloalkyl, perhaloalkyl, alkoxy, haloalkoxy, perhaloalkoxy, alkenyl, alkynyl, alkoxy, alkenoxy, acyl, acyloxy, acylamino, monosubstituted or disubstituted amino, carboxylic acid and its derivatives such as esters and amides, carbonylamino, hydroxyalkyl, aminoalkyl, alkoxyalkyl, alkylthio, thioalkyl, alkoxycarbonylamino, aminocarbonylamino, alkylaminocarbonylamino, alkoxyamino, hydroxyl amino groups; preferably, the substituents on 'A' may be selected from halogen, hydroxyl, thio, nitro, amino, cyano, optionally substituted groups selected from linear or branched alkyl, alkoxy, thioalkyl, haloalkyl, haloalkoxy, acyl, aminoalkyl groups;

The substituents on 'Ar' may be selected from hydroxy, halo, thio, nitro, amino, cyano, formyl, or optionally substituted groups selected from amidino, linear or branched alkyl, haloalkyl, perhaloalkyl, alkoxy, haloalkoxy, perhaloalkoxy, alkenyl, alkynyl, alkoxy, alkenoxy, monosubstituted or disubstituted amino, carboxylic acid and its derivatives such as esters and amides, carbonylamino, hydroxyalkyl, aminoalkyl, alkoxyalkyl, alkylthio, thioalkyl, alkylsulfonylamino, alkylsulfonyloxy, alkoxycarbonylamino, hydroxyl amino, sulfenyl derivatives, sulfonyl derivatives, sulfonic acid and its derivatives; preferably the substituents on 'Ar' may be selected from hydroxy, halo, amino or optionally substituted groups selected from linear or branched alkyl, monosubstituted or disubstituted amino, alkoxy, acyl, alkylthio, arylthio, alkylsulfonylamino, alkylsulfonyloxy, carboxylic acid and its derivatives such as esters and amides;

The substituents on 'A', or 'Ar' may further be optionally substituted by any of the groups as mentioned above.

In a preferred embodiment the groups, radicals described above may be selected from:

the "alkyl" group used either alone or in combination with other radicals, denotes a linear or branched radical containing one to eight carbons, selected from methyl, ethyl, n-propyl, iso-propyl, n-butyl, sec-butyl, tert-butyl, amyl, t-amyl, n-pentyl, n-hexyl, iso-hexyl, heptyl, octyl and the like;

the "alkenyl" group used either alone or in combination with other radicals, is selected from a radical containing from two to twelve carbons, more preferably groups selected from vinyl, allyl, 2-butenyl, 3-butenyl, 2-pentenyl, 3-pentenyl, 4-pentenyl, 2-hexenyl, 3-hexenyl, 4-hexenyl, 5-hexenyl, 2-heptenyl, 3-heptenyl, 4-heptenyl, 5-heptenyl, 6-heptenyl and the like; the "alkenyl" group includes dienes and trienes of straight and branched chains;

the "alkynyl" group used either alone or in combination with other radicals, is selected from a linear or branched radical containing two to twelve carbon atoms, more preferably thynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 3-hexynyl, 4-hexynyl, 5-hexynyl, and the like. The term "alkynyl" includes di- and tri-ynes;

the "cycloalkyl" or "alicyclic" group used either alone or in combination with other radicals, is selected from a cyclic radical containing three to seven carbons, more preferably cyclopropyl, cyclobutyl, cyclopentyl, cyclohexyl, cycloheptyl and the like;

the "cycloalkenyl" group used either alone or in combination with other radicals, are preferably selected from cyclopropenyl, 1-cyclobutenyl, 2-cylobutenyl, 1-cyclopentenyl, 2-cyclopentenyl, 3-cyclopentenyl, 1-cyclohexenyl, 2-cyclohexenyl, 3-cyclohexenyl, 1-cycloheptenyl, cycloheptadienyl, cycloheptatrienyl, and the like;

the "alkoxy" group used either alone or in combination with other radicals, is selected from groups containing an alkyl radical, as defined above, attached directly to an oxygen atom, more preferably groups selected from methoxy, ethoxy, n-propoxy, iso-propoxy, n-butoxy, t-butoxy, iso-butoxy, pentyloxy, hexyloxy, and the like;

the "alkenoxy" group used either alone or in combination with other radicals, is selected from groups containing an alkenyl radical, as defined above, attached to an oxygen atom, more preferably selsected from vinyloxy, allyloxy, butenoxy, pentenoxy, hexenoxy, and the like;

the "haloalkyl" group is selected from an alkyl radical, as defined above, suitably substituted with one or more halogens; such as perhaloalkyl, more preferably, perfluoro($C_1$-$C_6$)alkyl such as fluoromethyl, difluoromethyl, trifluoromethyl, fluoroethyl, difluoroethyl, trifluoroethyl, mono or polyhalo substituted methyl, ethyl, propyl, butyl, pentyl or hexyl groups;

the "haloalkoxy" group is selected from suitable haloalkyl, as defined above, directly attached to an oxygen atom, more preferably groups selected from fluoromethoxy, chloromethoxy, fluoroethoxy chloroethoxy and the like;

the "perhaloalkoxy" group is selected from a suitable perhaloalkyl radical, as defined above, directly attached to an oxygen atom, more preferably groups selected from trifluoromethoxy, trifluoroethoxy, and the like;

the "aryl" or "aromatic" group used either alone or in combination with other radicals, is selected from a suitable aromatic system containing one, two or three rings wherein such rings may be attached together in a pendant manner or may be fused, more preferably the groups are selected from phenyl, naphthyl, tetrahydronaphthyl, indane, biphenyl, and the like;

the "heterocyclyl" or "heterocyclic" group used either alone or in combination with other radicals, is selected from suitable saturated, partially saturated or unsaturated aromatic or non aromatic mono, bi or tricyclic radicals, containing one or more heteroatoms selected from nitrogen, sulfur and oxygen, more preferably selected from aziridinyl, azetidinyl, pyrrolidinyl, imidazolidinyl, piperidinyl, piperazinyl, 2-oxopiperidinyl, 4-oxopiperidinyl, 2-oxopiperazinyl, 3-oxopiperazinyl, morpholinyl, thiomorpholinyl, 2-oxomorpholinyl, azepinyl, diazepinyl, oxapinyl, thiazepinyl, oxazolidinyl, thiazolidinyl, dihydrothiophene, dihydropyran, dihydrofuran, dihydrothiazole, benzopyranyl, benzopyranonyl, benzodihydrofuranyl, benzodihydrothienyl, pyrazolopyrimidonyl, azaquinazolinoyl, thienopyrimidonyl, quinazolonyl, pyrimidonyl, benzoxazinyl, benzoxazinonyl, benzothiazinyl, benzothiazinonyl, thieno piperidinyl, and the like;

the "heteroaryl" or "heteroaromatic" group used either alone or in combination with other radicals, is selected from suitable single or fused mono, bi or tricyclic aromatic heterocyclic radicals containing one or more hetero atoms selected from O, N or S, more preferably the groups are selected from pyridyl, thienyl, furyl, pyrrolyl, oxazolyl, thiazolyl, isothiazolyl, imidazolyl, isoxazolyl, oxadiazolyl, thiadiazolyl, triazolyl, tetrazolyl, benzofuranyl, benzothienyl, indolinyl, indolyl, azaindolyl, azaindolinyl, pyrazolopyrimidinyl, azaquinazolinyl, pyridofuranyl, pyridothienyl, thienopyrimidyl, quinolinyl, pyrimidinyl, pyrazolyl, quinazolinyl, pyridazinyl, triazinyl, benzimidazolyl, benzotriazolyl, phthalazynil, naphthylidinyl, purinyl, carbazolyl, phenothiazinyl, phenoxazinyl, benzoxazolyl, benzothiazolyl and the like;

the "the groups "heteroaryloxy", "heteroaralkoxy", "heterocycloxy", "heterocylylalkoxy" are selected from suitable heteroaryl, heteroarylalkyl, heterocyclyl, heterocylylalkyl groups respectively, as defined above, attached to an oxygen atom;

the "acyl" group used either alone or in combination with other radicals, is selected from a radical containing one to eight carbons, more preferably selected from formyl, acetyl, propanoyl, butanoyl, iso-butanoyl, pentanoyl, hexanoyl, heptanoyl, benzoyl and the like, which may be substituted;

the "acyloxy" group used either alone or in combination with other radicals, is selected from a suitable acyl group, as defined above, directly attached to an oxygen atom, more preferably such groups are selected from acetyloxy, propionyloxy, butanoyloxy, iso-butanoyloxy, benzoyloxy and the like;

the "acylamino" group used either alone or in combination with other radicals, is selected from a suitable acyl group as defined earlier, attached to an amino radical, more preferably such groups are selected from $CH_3CONH$, $C_2H_5CONH$, $C_3H_7CONH$, $C_4H_9CONH$, $C_6H_5CONH$ and the like, which may be substituted;

the "mono-substituted amino" group used either alone or in combination with other radicals, represents an amino group substituted with one group selected from ($C_1$-$C_6$) alkyl, substituted alkyl, aryl, substituted aryl or arylalkyl groups as defined earlier, more preferably such groups are selected from methylamine, ethylamine, n-propylamine, n-butylamine, n-pentylamine and the like;

the 'disubstituted amino" group used either alone or in combination with other radicals, represents an amino group, substituted with two radicals that may be same or different selected from ($C_1$-$C_6$)alkyl, substituted alkyl, aryl, substituted aryl, or arylalkyl groups, as defined above, more preferably the groups are selected from dimethylamino, methylethylamino, diethylamino, phenylmethyl amino and the like;

the "arylamino" used either alone or in combination with other radicals, represents an aryl group, as defined above, linked through amino having a free valence bond from the nitrogen atom, more preferably the groups are selected from phenylamino, naphthylamino, N-methyl anilino and the like;

the "oxo" or "carbonyl" group used either alone (—C=O—) or in combination with other radicals such as alkyl described above, for e.g. "alkylcarbonyl", denotes a carbonyl radical (—C=O—) substituted with an alkyl radical described above such as acyl or alkanoyl;

the "carboxylic acid" group, used alone or in combination with other radicals, denotes a —COOH group, and includes derivatives of carboxylic acid such as esters and amides;

the "ester" group used alone or in combination with other radicals, denotes —COO— group, and includes carboxylic acid derivatives, more preferably the ester moieties are selected from alkoxycarbonyl, such as methoxycarbonyl, ethoxycarbonyl, and the like, which may optionally be substituted; aryloxycarbonyl group such as phenoxycarbonyl, napthyloxycarbonyl, and the like, which may optionally be substituted; aralkoxycarbonyl group such as benzyloxycarbonyl, phenethyloxycarbonyl, napthylmethoxycarbonyl, and the like, which may optionally be substituted; heteroaryloxycarbonyl, heteroaralkoxycarbonyl, wherein the heteroaryl group, is as defined above, which may optionally be substituted; heterocyclyloxycarbonyl, where the heterocyclic group, as defined earlier, which may optionally be substituted;

the "amide" group used alone or in combination with other radicals, represents an aminocarbonyl radical ($H_2N$—C=O—), wherein the amino group is mono- or di-substituted or unsubstituted, more preferably the groups are selected from methylamide, dimethylamide, ethylamide, diethylamide, and the like;

the "aminocarbonyl" group used either alone or in combination with other radicals, may be selected from 'aminocarbonyl', 'aminocarbonylalkyl", "n-alkylaminocarbonyl", "N-arylaminocarbonyl", "N,N-dialkylaminocarbonyl", "N-alkyl-N-arylaminocarbonyl", "N-alkyl-N-hydroxyaminocarbonyl", and "N-alkyl-N-hydroxyaminocarbonylalkyl", each of them being optionally substituted. The terms "N-alkylaminocabonyl" and "N,N-dialkylaminocarbonyl" denotes aminocarbonyl radicals, as defined above, which have been substituted with one alkyl radical and with two alkyl radicals, respectively. Preferred are "lower alkylaminocarbonyl" having lower alkyl radicals as described above attached to aminocarbonyl radical. The terms "N-arylaminocarbonyl" and "N-alkyl-N-arylaminocarbonyl" denote amiocarbonyl radicals substituted, respectively, with one aryl radical, or one alkyl, and one aryl radical. The term "aminocarbonylalkyl" includes alkyl radicals substituted with aminocarbonyl radicals;

the "hydroxyalkyl" group used either alone or in combination with other radicals, is selected from an alkyl group, as defined above, substituted with one or more hydroxy radicals, more preferably the groups are selected from hydroxymethyl, hydroxyethyl, hydroxypropyl, hydroxybutyl, hydroxypentyl, hydroxyhexyl and the like;

the "aminoalkyl" group used alone or in combination with other radicals, denotes an amino (—$NH_2$) moiety attached to an alkyl radical, as defined above, which may be substituted, such as mono- and di-substituted aminoalkyl. The term "alkylamino" used herein, alone or in combination with other radicals, denotes an alkyl radical, as defined above, attached to an amino group, which may be substituted, such as mono- and di-substituted alkylamino;

the "alkoxyalkyl" group used alone or in combination with other radicals, denotes an alkoxy group, as defined above, attached to an alkyl group as defined above, more preferably the groups may be selected from methoxymethyl, ethoxymethyl, methoxyethyl, ethoxyethyl and the like;

the "alkylthio" group used either alone or in combination with other radicals, denotes a straight or branched or cyclic monovalent substituent comprising an alkyl group as defined above, linked through a divalent sulfur atom having a free valence bond from the sulfur atom, more preferably the groups may be selected from methylthio, ethylthio, propylthio, butylthio, pentylthio and the like or cyclic alkylthio selected from cyclopropylthio, cyclobutylthio, cyclopentylthio, cyclohexylthio and the like, which may be optionally substituted;

the "thioalkyl" group used either alone or in combination with other radicals, denotes an alkyl group, as defined above, attached to a group of formula —SR', where R' represents hydrogen, alkyl or aryl group, e.g. thiomethyl, methylthiomethyl, phenylthiomethyl and the like, which may be optionally substituted.

the "alkoxycarbonylamino" group used alone or in combination with other radicals, is selected from a suitable alkoxycarbonyl group, as defined above, attached to an amino group, more preferably methoxycarbonylamino, ethoxycarbonylamino, and the like;

the "aminocarbonylamino", "alkylaminocarbonylamino", "dialkylaminocarbonylamino" groups used alone or in combination with other radicals, is a carbonylamino (—$CONH_2$) group, attached to amino($NH_2$), alkylamino group or dialkylamino group respectively, where alkyl group is as defined above;

the "amidino" group used either alone or in combination with other radicals, represents a —C(=NH)—$NH_2$ radical; the "alkylamidino" group represents an alkyl radical, as described above, attached to an amidino group;

the "hydrazino" group used either alone or in combination with other radicals, represents a group of the formula —NHNH—, suitably substituted with other radicals, selected from those described above such as an alkyl hydrazino, where an alkyl group, as defined above is attached to a hydrazino group;

the "alkoxyamino" group used either alone or in combination with other radicals, represents a suitable alkoxy group as defined above, attached to an amino group;

the "hydroxyamino" group used either alone or in combination with other radicals, represents a —NHOH moiety, and may be optionally substituted with suitable groups selected from those described above;

the "sulfenyl" group or "sulfenyl derivatives" used alone or in combination with other radicals, represents a bivalent group, —SO— or $R_xSO$, where $R_x$ is an optionally substituted alkyl, aryl, heteroaryl, heterocyclyl, group selected from those described above;

the "sulfonyl" group or "sulfones derivatives" used either alone or in combination with other radicals, with other terms such as alkylsulfonyl, represents a divalent radical —$SO_2$—, or $R_xSO_2$—, where $R_x$ is as defined above. More preferably, the groups may be selected from "alkylsulfonyl" wherein suitable alkyl radicals, selected from those defined above, is attached to a sulfonyl radical, such as methylsulfonyl, ethylsulfonyl, propylsulfonyl and the like, "arylsulfonyl" wherein an aryl radical, as defined above, is attached to a sulfonyl radical, such as phenylsulfonyl and the like.

Suitable groups and substituents on the groups may be selected from those described anywhere in the specification.

Particularly useful compounds of the present invention are:

4-Chloro-N-{[8-chloro-1- (2,4-dichloro-phenyl)-1,4,5,6-tetrahydro-1,2-diaza-benzo [e] azulene-3-yl]-methylaminomethylene}-benzenesulfonamide and its pharmaceutically acceptable salts;

8-chloro-1-(2,4-dichloro-phenyl)-4,5-dihydro-1H-6-oxa-1,2-diaza-benzo [e] azulene-3-carboxylic acid piperidin-1-ylamide and its pharmaceutically acceptable salts;

8-chloro-1-(2,4-dichloro-phenyl)-4,5-dihydro-1H-6-oxa-1,2-diaza-benzo [e] azulene-3-carboxylic acid -4-hydroxy-piperidin-1-yl -amide and its pharmaceutically acceptable salts;

8-chloro-1-(2,4-dichloro-phenyl)-4,5-dihydro-1H-6-oxa-1,2-diaza-benzo [e] azulene-3-carboxylic acid pyrrolidin-1-yl amide and its pharmaceutically acceptable salts;

8-chloro-1-(2,4-dichloro-phenyl)-4,5-dihydro-1H-6-oxa-1,2-diaza-benzo [e] azulene-3-carboxylic acid (hexahydro-cyclopenta[c] pyrrol-2-yl)-amide and its pharmaceutically acceptable salts;

8-chloro-1-(2,4-dichloro-phenyl)-4,5-dihydro-1H-6-oxa-1,2-diaza-benzo [e] azulene-3-carboxylic acid morpholine-4-yl-amide and its pharmaceutically acceptable salts;

8-chloro-1-(2,4-dichloro-phenyl)-4,5-dihydro-1H-6-oxa-1,2-diaza-benzo [e] azulene-3-carboxylic acid (4-methyl-piperazine-1-yl)-amide and its pharmaceutically acceptable salts;

8-chloro-1-(4-chloro-phenyl)-4,5-dihydro-1H-6-oxa-1,2-diaza-benzo [e] azulene-3-carboxylic acid piperidin-1-ylamide and its pharmaceutically acceptable salts;

8-chloro-1-(4-chloro-phenyl)-4,5-dihydro-1H-6-oxa-1,2-diaza-benzo [e] azulene-3-carboxylic acid pyrrolidin-1-ylamide and its pharmaceutically acceptable salts;

8-chloro-1-(4-chloro-phenyl)-4,5-dihydro-1H-6-oxa-1,2-diaza-benzo [e] azulene-3-carboxylic acid morpholin-4-ylamide and its pharmaceutically acceptable salts;

8-chloro-1-(4-chloro-phenyl)-4,5-dihydro-1H-6-oxa-1,2-diaza-benzo [e] azulene-3-carboxylic acid N'-cyclopropyl-hydrazide and its pharmaceutically acceptable salts;

8-chloro-1-(4-chloro-phenyl)-4,5-dihydro-1H-6-oxa-1,2-diaza-benzo [e] azulene-3-carboxylic acid piperidin-1-ylamide and its pharmaceutically acceptable salts;

1-(2,4-Dichloro-phenyl)-8-methyl-4,5-dihydro-1H-6-oxa-1,2-diaza-benzo [e] azulene-3-carboxylic acid piperidin-1-ylamide and its pharmaceutically acceptable salts;

1-(2,4-Dichloro-phenyl)-8-methyl-4,5-dihydro-1H-6-oxa-1,2-diaza-benzo [e] azulene-3-carboxylic acid pyrrolidin-1-ylamide and its pharmaceutically acceptable salts;

1-(4-chloro-phenyl)-8-methyl-4,5-dihydro-1H-6-oxa-1,2-diaza-benzo [e] azulene-3-carboxylic acid piperidin-1-ylamide and its pharmaceutically acceptable salts;

1-{[8-chloro-1-(2,4-dichloro-phenyl)-1,4,5,6-tetrahydro-7-thia-1,2-diaza-cyclopenta [e] azulene-3-carboxylic acid piperidin-1-ylamide and its pharmaceutically acceptable salts;

8-Chloro-1-(2,4-dichloro-phenyl)-1,4,5,6-tetrahydro-7-thia-1,2-diaza-cyclopenta [e] azulene-3-carboxylic acid (hexahydro-cyclopenta [c] pyrrol-2-yl)-amide and its pharmaceutically acceptable salts;

8-Chloro-1-(2,4-dichloro-phenyl)-4,5-dihydro-1H-6,7-dithia-1,2-diaza-cyclopenta[e]azulene-3-carboxylic acid piperidin-1-ylamide and its pharmaceutically acceptable salts;

7-Chloro-1-(2,4-dichloro-phenyl)-1,5-dihydro-4,6-dithia-1,2-diaza-as-indacene-3-carboxylic acid piperidin-1-ylamide and its pharmaceutically acceptable salts;

7-Chloro-1-(2,4-dichloro-phenyl)-1,5-dihydro-4,6-dithia-1,2-diaza-as-indacene-3-carboxylic acid (hexahydro-cyclopenta [c] pyrrol-2-yl)-amide and its pharmaceutically acceptable salts;

8-Chloro-1-(2,4-dichloro-phenyl)-4,5-dihydro-1H-6-thia-1,2-diaza-benzo [e] azulene-3-carboxylic acid piperidin-1-ylamide and its pharmaceutically acceptable salts;

8-Bromo-1-(2,4-dichloro-phenyl)-4,5-dihydro-1H-6-oxa-1,2-diaza-benzo [e] azulene-3-carboxylic acid piperidin-1-ylamide and its pharmaceutically acceptable salts;

The compounds of the present invention may be prepared using the methods described below, together with conventional techniques known to those skilled in the art of organic synthesis, or variations thereon as appreciated by those skilled in the art.

Referred methods include, but are not limited to those described below, where all symbols are as defined earlier.

Scheme:

Compound of formula 2 by suitable modification of similar processes described earlier in the art [*Chem. Pharm. Bull.* 2002, 50, 1109-1113]. Compound of formula 4 may be prepared by refluxing 2 with suitable substituted hydrazine hydrochloride of formula 3, where 'Ar' is as defined earlier, in suitable solvents such as MeOH, EtOH, propanol, isopropanol, butanol, t-butanol, acetic acid and the like or mixtures thereof. Alkaline hydrolysis of 4 using suitable bases like NaOH, KOH, LiOH, AgNO$_3$, Na$_2$CO$_3$, CSCO$_3$ and the like in solvents such as methanol, methanol/water, methanol/THF or THF/H$_2$O and the like or mixtures thereof gives the corresponding acid of formula 5. Compounds of formula 5 is first converted to their corresponding acid chloride by treating with suitable halogenating agents selected from SOCl$_2$, COCl$_2$, PCl$_3$, PCl$_5$ and the like in suitable solvents such toluene, benzene, xylene, dichloromethane, chloroform and the like or mixtures thereof. The acid chlorides generated in situ may be subsequently treated with suitable substituted or unsubstituted amines, bicyclic amines, substituted or unsubstituted hydrazines, to obtain compounds of formula (I).

The compound of formula 5 may optionally, after conversion to its corresponding acid chloride be treated with suitable compounds of formula 6, where 'Q' is as defined earlier, in solvents selected from triethyl amine, DMSO, DMF, diisopropyl ethyl amine and the like or mixtures thereof to obtain the compounds of formula 7.

The compound of formula 7 on treatment with suitable halogenating agent such as SOCl$_2$, COCl$_2$, PCl$_3$, PCl$_5$ and the like in suitable solvents such toluene, benzene, xylene, dichloromethane, chloroform and the like or mixtures thereof to provide compounds of formula 8. The compound of formula 8 is stirred with suitable amines of formula NHR$_2$R$_3$, where R$_2$ & R$_3$ are as defined earlier, in solvents selected from methanol, ethanol, water, THF and the like to obtain compounds of formula (I).

Scheme:

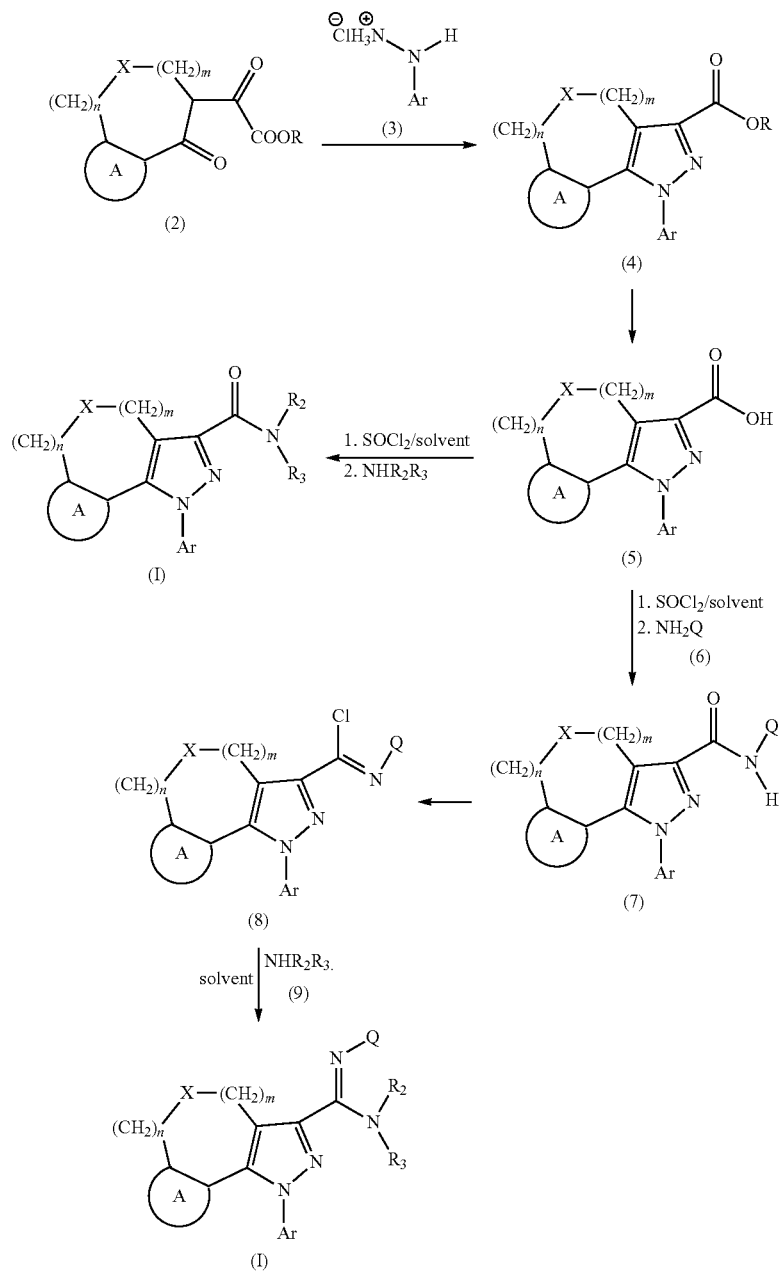

The compounds of formula (I) may be optionally converted to their suitable pharmaceutically acceptable salts by suitable modifications of techniques and processes known to persons skilled in the art.

It will be appreciated that in any of the above mentioned reactions any reactive group in the substrate molecule may be protected, according to conventional chemical practice. Suitable protecting groups in any of the above mentioned reactions are those used conventionally in the art. The methods of formation and removal of such protecting groups are those conventional methods appropriate to the molecule being protected. T. W. Greene and P. G. M. Wuts "Protective groups in Organic Synthesis", John Wiley & Sons, Inc, 1999, 3$^{rd}$ Ed., 201-245 along with references therein gives such conventional methods and are incorporated herein as references.

The novel compounds of the present invention can be formulated into suitable pharmaceutically acceptable compositions by combining with suitable excipients as are well known.

The compounds of Formula (I) or pharmaceutical compositions containing them may be administered either by oral, topical or parenteral administration.

The pharmaceutical composition is provided by employing conventional techniques. Preferably the composition is in unit dosage form containing an effective amount of the active component, that is, the compounds of formula (I) according to this invention.

The quantity of active component, that is, the compounds of formula (I) according to this invention, in the pharmaceutical composition and unit dosage form thereof may be varied or adjusted widely depending upon the particular application method, the potency of the particular compound and the desired concentration. Generally, the quantity of active component will range between 0.5% to 90% by weight of the composition.

The invention is explained in greater detail by the examples given below, which are provided by way of illustration only and therefore should not be construed to limit the scope of the invention.

It will be appreciated that one or more of the processes described in the general schemes above may be used to prepare the compounds of the present invention.

1H NMR spectral data given in the tables (vide infra) are recorded using a 300 MHz spectrometer (Bruker AVANCE-300) and reported in δ scale. Until and otherwise mentioned the solvent used for NMR is $CDCl_3$ using tetramethyl silane as the internal standard.

EXAMPLE 1

4-Chloro-N-{[8-chloro-1-(2,4-dichloro-phenyl)-1,4,5,6-tetrahydro-1,2-diaza-benzo [e] azulene-3-yl]-methylamino-methylene}-benzenesulfonamide.

8-chloro-1-(2,4-dichloro-phenyl)-1,4,5,6-tetrahydro-1,2-diaza-benzo [e] azulene-3-carboxylic acid was prepared by by suitable modifications of similar techniques and processes known in the art.

Step A:
4-Chloro-N {8-chloro-1-(2,4-dichloro-phenyl)-1,4,5,6-tetrahydro-1,2-diaza-benzo [e] azulene-3-carbonyl}-benzene-sulfonamide 8-Chloro-1-(2,4-dichloro-phenyl)-1,4,5,6-tetrahydro-1,2-diaza-benzo [e] azulene-3-carboxylic acid (4.3 g, 10.55 mmol) was converted into acid chloride using thionyl chloride (2.31 mL, 31.66 mmol) in toluene by refluxing at ca. 110° C. over a period of 1 h.

The solvents were evaporated under reduced pressure. The residue obtained was taken in dichloromethane (20 mL) and the resulting solution was added to the cooled suspension of 4-chloro benzene sulfonamide (2.7 g, 4.137 mmol) and TEA (1.97 mL, 14.137 mmol) in dichloromethane (50 mL). The reaction mixture was stirred at ca. 27° C. over a period of 30 min and diluted with water (150 mL), extracted with dichloromethane.

The organic layer was separated, dried over anhydrous $Na_2SO_4$ and evaporated under reduced pressure to afford crude colorless oil. The oil was purified through column chromatography to afford 4-Chloro-N-{8-chloro-1-(2,4-dichloro-phenyl)-1,4, 5,6-tetrahydro-1,2-diaza-benzo [e] azulene-3-carbonyl}-benzene-sulfonamide (4.75 g, 8.175 mmol) as off white solid.

$^1$HNMR ($CDCl_3$, 300 MHz): δ 9.38(s, 1H), 8.0(d, J=8.4 Hz, 2H), 7.5(d, J=8.4 Hz, 2H), 7.4(m, 3H), 7.2(dd, J=9.9, 8.4 Hz, 1H), 6.9(dd, J=6.3, 1.9 Hz, 1H), 6.5(d, J=8.4 Hz, 1H), 2.6(t, J=6.6, 6.3 Hz, 2H), 2.2(br, 2H) 1.26(br, 2H).

Step B:
4-Chloro-N-{[8-chloro-1- (2,4-dichloro-phenyl)-1,4,5,6-tetrahydro-1,2-diaza-benzo [e] azulene-3-yl]-methylamino-methylene}-benzenesulfonamide
(Compound 1)
4-Chloro-N-{8-chloro-1-(2,4-dichloro-phenyl)-1,4,5,6-tetrahydro-1,2-diaza-benzo [e] azulene-3-carbonyl}-benzene-sulfonamide (2.0 g, 3.44 mmol) and $PCl_5$ (1.56 g, 6.88 mmol) in chlorobenzene (20 mL) were refluxed at ca. 120° C. over a period of 3.0 h. The solvents were evaporated under reduced pressure to afford yellow gummy solid. The gummy solid was taken in dichloromethane (15 mL) and cooled to 0-5° C. To this cooled solution, 40% aq. monomethyl amine solution (5.0 mL) was added and stirred at ca. 29° C. over a period of 1 h. The reaction mixture was diluted with water (100 mL) and extracted with dichloromethane. The organic layer was separated, dried over anhydrous $Na_2SO_4$ and evaporated under reduced pressure to afford yellow oil. The oil was purified through column chromatography to afford 4-Chloro-N-{[8-chloro-1-(2,4-dichloro-phenyl)-1,4,5,6-tetrahydro-1,2-diaza-benzo [e] azulene-3-yl]-methylamino-methylene}-benzene sulfonamide (0.175 g, 0.294 mmol) as title compound 1, a white solid.

$^1$HNMR: ($CDCl_3$, 300 MHz) δ 7.8 (d, J=7.5 Hz, 2H), 7.4 (d, J=7.5 Hz, 2H), 7.39 (d, J=8.4 Hz, 1H), 7.34 (d, J=1.8 Hz, 1H), 7.3 (m, 2H), 7.0 (d, J=8.4 Hz, 1H), 6.5 (d, J=5.4 Hz, 1H), 3.27 (d, J=5.1 Hz, 2H), 3.18 (d, J=5.1 Hz, 1H), 2.6 (m, 3H), 1.5 (s, 3H).

EXAMPLE 2

Hydrochloride Salt of 8-chloro-1-(2,4-dichloro-phenyl)-4,5-dihydro-1H-6-oxa-1,2-diaza-benzo [e] azulene-3-carboxylic acid piperidin-1-ylamide.

a) 8-Chloro-1-(2,4-dichloro-phenyl)-4,5-dihydro-1H-6-oxa-1,2-diaza-benzo [e] azulene-3-carboxylic acid by suitable modifications of similar techniques and processes known in the art.

b) Hydrochloride salt of 8-Chloro-1-(2,4-dichloro-phenyl)-4,5-dihydro-1H-6-oxa 1, 2-diaza-benzo [e] azulene-3-carboxylic acid piperidin-1- yl- amide (Compound 2). 8-chloro-1- (2,4-dichloro-phenyl)-4,5-dihydro-1H-6-oxa 1,2-diaza-benzo [e] azulene-3-carboxylic acid (0.500 g, 1.221 mmol) was coupled with 1-amino-piperidine (0.197 mL, 1.832 mmol) in presence of 1-Hydroxy-benzotriazole monohydrate (HOBt. $H_2O$), 1-(3-Dimethylaminopropyl)-3-ethylcarbodiimide hydrochloride (EDC-HCl) and TEA in dichloromethane (25 mL) at ca. 27° C. over a period of 25-30 min. The reaction was diluted with $H_2O$ (30 mL) and extracted with dichloromethane. The dichloromethane layer was separated, dried over anhydrous $Na_2SO_4$ and evaporated under reduced pressure to afford brown oil. The brown oil was taken in anhydrous methanol and treated with ethereal HCl (ca. 4 mL) at 0-5° C. Solvents were removed under reduced pressure and residue was triturated in ethyl acetate to afford solid. The solid was filtered, washed with diethyl ether to afford title compound 2 (0.435 g, 0.824 mmol) as light brown solid. $^1$HNMR: ($CDCl_3$, 300 MHz) δ 9. 35 (s, 1H), 7.51 (d, J=1.74 Hz, 1H), 7.40 (m, 2H), 7.34 (m, 1H), 7.14 (d, J=1.95 Hz, 1H), 6.62 (d, J=8.55 Hz, 1H), 4.38 (m, 2H), 4.06 (bs, 3H), 3.48. (bs, 3H), 3.26 (m, 2H), 3.11 (m, 2H), 1.67(bs, 4H), 1.41(m, 1H), 1.18 (m, 1H).

(DMSO-$D_6$, 300 MHz) δ 10.53 (s, 1H), 7.89 (d, J=2.01 Hz, 1H), 7.78 (d, J=8.49 Hz, 1H), 7.68 (dd, J=10.47, 1.95 Hz, 1H), 7.26 (d, J=1.95 Hz, 1H), 7.03 (dd, J=10.56, 1.95 Hz, 1H), 6.72 (d, J=8.61 Hz, 1H), 4.45 (bs, 1H), 4.25 (bs, 1H), 3.23 (bs, 4H), 3.06 (m, 3H), 1.72 (bs, 4H), 1.42(bs, 2H), 1.16(t, 1H), 0.98 (t, 1H).

Following compounds were prepared by suitable modifications, variations of reactants, reaction conditions, reaction steps of the processes described for the synthesis of compound 2.

Compound 3:
Hydrochloride salt of 8-chloro-1-(2,4-dichloro-phenyl)-4,5-dihydro-1H-6-oxa-1,2-diaza-benzo [e] azulene-3-carboxylic acid -(4-hydroxy-piperidin-1-yl-amide.

¹HNMR: (CDCl₃, 300 MHz) δ 10.26 (bs, 1H), 7.9 (d, J=2.1 Hz, 1H), 7.7 (d, J=8.4 Hz, 1H), 7.6 (dd, J=1.8 Hz, 1H), 7.2 (d, J=1.8 Hz, 1H), 7.0 (dd, J=6.8, 2.1 Hz, 1H), 3.38 (bs, 2H), 3.21 (bs, 4H), 3.0(bs, 4H), 2.7 (bs, 2H).

Compound 4:

Hydrochloride salt of 8-chloro-1-(2,4-dichloro-phenyl)-4,5-dihydro-1H-6-oxa-1,2-diaza-benzo [e] azulene-3-carboxylic acid pyrrolidin-1-yl amide.

¹HNMR: (CDCl₃, 300 MHz) δ 8.70 (dd, J=6.66 Hz, 1H), 7.90 (m, 1H), 7.71 (dd, J=6.33, 2.19 Hz, 1H), 7.26 (d, J=2.10 Hz, 1H), 7.03 (dd, J=6.45, 2.16 Hz, 1H), 6.72 (d, J=8.55 Hz, 1H), 4.47 (m, 1H), 4.25 (m, 2H), 1.90-1.80(bs, 6H), 1.79 (m, 1H), 1.23-1.15 (m, 1H).

Compound 5:

Hydrochloride salt of 8-chloro-1-(2, 4-dichloro-phenyl)-4,5-dihydro-1H-6-oxa-1,2-diaza-benzo [e] azulene-3-carboxylic acid (hexahydro-cyclopenta[c] pyrrol-2-yl)-amide.

¹HNMR: (CDCl₃, 300 MHz) δ 9.24 (s, 1H), 7.60 (s, 1H), 7.51 (m, 2H), 7.15 (d, J=1.86 Hz, 2H), 6.82 (m, 1H), 6.62 (d, J=8.49 Hz, 1H), 4.45 (bs, 2H), 3.96 (bs, 3H), 3.71 (bs, 2H), 3.38 (bs, 2H), 3.27 (bs, 2H), 1.73(bs, 6H).

(DMSO-D₆) δ 11.03 (s, 1H), 7.90 (d, J=1.86 Hz, 1H), 7.79 (d, J=8.52 Hz, 1H), 7.70 (dd, J=10.41, 1.89 Hz, 1H), 7.26 (d, J=1.83 Hz, 1H), 7.04 (dd, J=10.41, 1.83 Hz, 1H), 6.73 (d, J=8.58 Hz, 1H), 4.50 (bs, 1H), 4.25 (bs, 2H), 3.69 (bs, 2H), 3.45 (m, 1H), 3.40 (m, 1H), 3.06 (bs, 2H), 2.96 (bs, 2H), 1.71 (bs, 4H), 1.62 (bs, 2H).

Compound 6

Hydrochloride salt of 8-chloro-1-(2,4-dichloro-phenyl)-4,5-dihydro-1H-6-oxa-1,2-diaza-benzo [e] azulene-3-carboxylic acid morpholine-4-yl-amide.

¹HNMR: (DMSO-D₆, 300 MHz) δ 9.4 (s, 1H), 7.8 (d, J=2.1 Hz, 1H), 7.7 (d, J=8.7 Hz, 1H), 7.6 (dd, J=6.3, 2.1 Hz, 1H), 7.2 (d, J=2.1 Hz, 1H), 7.0 (dd, J=6.4, 2.1 Hz, 1H), 6.7 (d, J=8.4 Hz, 1H), 4.4 (m, 1H), 4.2 (m, 1H), 3.6 (m, 4H), 2.8 (m, 4H), 1.22 (s, 2H).

Compound 7

Hydrochloride salt of 8-chloro-1-(2,4-dichloro-phenyl)-4,5-dihydro-1H-6-oxa-1,2-diaza-benzo [e] azulene-3-carboxylic acid (4-methyl-piperazine-1-yl)-amide. ¹HNMR: (DMSO-D₆, 300 MHz) δ 9.7 (s, 1H), 7.8 (d, J=2.1 Hz, 1H), 7.7 (d, J=8.7 Hz, 1H), 7.6 (dd, J=6.3, 2.1 Hz, 1H), 7.2 (d, J=2.4 Hz, 1H), 7.0 (dd, J=6.4, 2.1 Hz, 1H), 6.7 (d, J=8.4 Hz, 1H), 4.4 (m, 1H), 4.2 (m, 1H), 3.7 (m, 1H), 3.1 (bs, 4H), 2.7 (s, 3H), 1.22 (s, 4H).

Compound 8

Hydrochloride salt of 8-chloro-1-(4-chloro-phenyl)-4,5-dihydro-1H-6-oxa-1,2-diaza-benzo [e] azulene-3-carboxylic acid piperidin-1-ylamide.

¹HNMR: (DMSO-D₆, 300 MHz) δ 11.0 (s, 1H), 7.58 (d, J=8.4 Hz, 2H), 7.4 (d, J=8.7 Hz, 2H), 7.2 (d J=2.1 Hz, 1H), 7.0 (dd, J=6.6, 1.8 Hz, 1H), 6.7 (d, J=8.4 Hz, 1H), 4.3 (t, J=6.6 Hz, 2H), 3.1 (bs, 4H), 2.7 (d, J=4.8 Hz, 2H), 1.97 (bs, 4H), 1.4 (bs, 2H).

Compound 9

Hydrochloride salt of 8-chloro-1-(4-chloro-phenyl)-4,5-dihydro-1H-6-oxa-1,2-diaza-benzo [e] azulene-3-carboxylic acid pyrrolidin-1-ylamide.

¹HNMR: (DMSO-D₆, 300 MHz) δ 9.1 (s, 1H), 7.5 (d, J=8.7 Hz, 2H), 7.4 (d, J=8.7 Hz, 2H), 7.2 (d, J=2.1 Hz, 1H), 7.0 (dd, J=6.3, 2.1 Hz, 1H), 6.7 (d, J=8.4Hz, 1H), 4.3 (t, J=6.3 Hz, 2H), 3.1 (bs, 4H), 2.7 (d, J=4.8 Hz, 2H), 1.97 (bs, 4H), 1.4 (bs, 2H).

Compound 10

Hydrochloride salt of 8-chloro-1-(4-chloro-phenyl)-4,5-dihydro-1H-6-oxa-1,2-diaza-benzo [e] azulene-3-carboxylic acid morpholin-4-ylamide.

¹HNMR: (DMSO-D₆, 300 MHz) δ 9.5 (s, 1H), 7.5 (d, J=8.4 Hz, 2H), 7.4 (d, J=8.7 Hz, 2H), 7.2 (d, J=2.1 Hz, 1H), 7.0 (dd, J=6.6, 2.1 Hz, 1H), 6.7 (d, J=8.7 Hz, 1H), 4.3 (t, J=6.6 Hz, 2H), 3.2 (t, J=6.6 Hz, 2H), 3.0 (m, 2H), 2.8(m, 4H), 2.7 (m, 2H).

Compound 11

Hydrochloride salt of 8-chloro-1-(4-chloro-phenyl)-4,5-dihydro-1H-6-oxa-1,2-diaza-benzo [e] azulene-3-carboxylic acid —N'-cyclopropyl-hydrazide.

¹HNMR: (DMSO-D₆, 300 MHz) δ 10.7 (s, 1H), 8.3 (d, J=4.5 Hz, 1H), 7.7 (d, J=8.4 Hz, 1H), 7.6 (dd, J=6.3, 2.1 Hz, 1H), 7.2 (d, J=2.1 Hz, 1H), 7.0 (dd, J=6.6, 2.1 Hz, 1H), 6.7 (d, J=8.7 Hz, 1H), 4.4 (m, 4H), 4.0 (m, 4H), 2.8 (m, 2H), 0.5(m, 5H).

Compound 12

Hydrochloride salt of 8-chloro-1-(4-chloro-phenyl)-4,5-dihydro-1H-6-oxa-1,2-diaza-benzo [e] azulene-3-carboxylic acid piperidin-1-ylamide.

¹HNMR: (DMSO-D₆, 300 MHz) δ 10.66 (s, 1H), 7.52 (s, 3H), 7.39 (d, J=2.9 Hz, 2H), 7.27 (s, 1H), 6.99 (d, J=8.55 Hz, 1H), 4.40 (t, J=5.95 Hz, 2H), 3.56 (t, J=6.0 Hz, 3H), 3.18 (d, J=6.99 Hz, 4H), 1.74 (s, 3H), 1.43(s, 2H).

Compound 13

Hydrochloride salt of 1-(2, 4-Dichloro-phenyl)-8-methyl-4,5-dihydro-1H-6-oxa-1,2-diaza-benzo [e] azulene-3-carboxylic acid piperidin-1-yl amide.

¹HNMR: (CDCl₃, 300 MHz) δ 9.53 (s, 1H), 7.50 (s, 1H), 7.39(m, 2H), 6.91 (s, 1H), 6.64 (d, J=7.66 Hz, 1H), 6.56 (d, J=8.09 Hz, 1H), 4.13 (bs, 4H), 4.05 (bs, 4H), 3.48 (bs, 3H), 2.28 (s, 3H), 2.06 (s, 4H).

Compound 14

Hydrochloride salt of 1-(2,4-Dichloro-phenyl)-8-methyl-4,5-dihydro-1H-6-oxa-1,2-diaza-benzo [e] azulene-3-carboxylic acid pyrrolidin-1-ylamide.

¹HNMR: (CDCl₃, 300 MHz) δ 9.31(s, 1H), 7.51(s, 1H), 7.40(m, 2H), 6.91 (s, 1H), 6.58 (m, 2H), 4.36 (bs, 2H), 3.90 (bs, 4H), 3.39 (bs, 2H), 2.28 (bs, 6H). (DMSO-D₆) 11.70 (s, 1H), 7.99 (d, J=2.13 Hz, 1H), 7.75 (d, J=8.49 Hz, 1H), 7.68 (dd, J=8.52, 2.16 Hz, 1H), 6.95 (s, 1H), 6.71 (d, J=7.35 Hz, 1H), 6.59 (d, J=8.07 Hz, 1H), 4.4 (m, 1H), 4.21(m, 1H), 3.56 (bs, 1H), 3.34 (m, 2H), 2.21 (s, 3H), 1.21 (bs, 4H).

Compound 15

Hydrochloride salt of 1-(4-chloro-phenyl)-8-methyl-4,5-dihydro-1H-6-oxa-1,2-diaza-benzo [e] azulene-3-carboxylic acid piperidin-1-ylamide.

¹HNMR: (DMSO-D₆, 300 MHz) δ 11.15 (s, 1H), 7.58 (d, J=8.52 Hz, 1H), 7.40 (d, J=8.52 Hz, 2H), 6.99 (s, 1H), 6.75 (d, J=7.95 Hz, 1H), 6.63 (d, J=8.01 Hz, 1H), 4.30 (bs, 2H), 3.75 (t, 2H), 3.37 (s, 4H), 3.24 (t, 2H), 2.24 (s, 3H), 1.80 (s, 4H), 1.46 (m, 2H).

Compound 16

Hydrochloride salt of 1-([8-chloro-1-(2,4-dichloro-phenyl)-1,4,5,6-tetrahydro-7-thia-1,2-diaza-cyclopenta [e] azulene-3-carboxylic acid piperidin-1-ylamide.

¹HNMR: (CDCl₃, 300 MHz) δ 9.4 (s, 1H), 7.60 (s, 1H), 7.4 (d, 2H), 5.9 (s, 1H), 3.9 (bs, 5H), 3.1 (s, 3H), 2.9 (t, 2H), 2.1 (bs, 6H).

Compound 17

Hydrochloride salt of 8-Chloro-1-(2,4-dichloro-phenyl)-1,4,5,6-tetrahydro-7-thia-1,2-diaza-cyclopenta [e] azulene-3-carboxylic acid (hexahydro-cyclopenta [c] pyrrol-2-yl)-amide.

¹HNMR: (CDCl₃, 300 MHz) δ 9.4 (s, 1H), 7.50 (s, 1H), 7.4 (d, 2H), 5.9 (s, 1H), 4.4 (bs, 2H), 3.9 (bs, 2H), 3.1 (s, 2H), 3.0 (bs, 2H), 2.8 (t, 2H), 2.0 (bs, 2H, 1.9-1.6 (m, 6H).

Compound 18
Hydrochloride salt of 8-Chloro-1-(2,4-dichloro-phenyl)-4,5-dihydro-1H-6,7-dithia-1,2-diaza-cyclopenta [e] azulene-3-carboxylic acid piperidin-1-ylamide.

$^1$HNMR: (CDCl$_3$, 300 MHz) δ 9.4 (s, 1H), 7.50 (s, 1H), 7.4 (d, 3H), 6.1 (s, 1H), 3.9 (bs, 4H), 3.4 (d, J=5.8 Hz, 2H), 3.2 (d, J=5.46 Hz, 2H), 2.1 (s, 6H).

Compound 19
Hydrochloride salt of 7-Chloro-1-(2,4-dichloro-phenyl)-1,5-dihydro-4,6-dithia-1,2-diaza-as-indacene-3-carboxylic acid piperidin-1-ylamide.

$^1$HNMR: (DMSO-D$_6$, 300 MHz) δ 10.62 (bs, 1H), 8.10 (s, 1H), 7.85 (d, J=8.49 HZ, 1H), 7.71 (dd, J=8.49, 2.1 Hz, 1H), 6.08 (s, 1H), 4.23 (s, 2H), 2.89 (m, 4H), 1.67 (m, 4H), 1.10 (m, 6H).

Compound 20
Hydrochloride salt of 7-Chloro-1-(2,4-dichloro-phenyl)-1,5-dihydro-4,6-dithia-1,2-diaza-as-indacene-3-carboxylic acid (hexahydro-cyclopenta [c] pyrrol-2-yl)-amide.

$^1$HNMR: (DMSO-D$_6$, 300 MHz) δ 11 (s, 1H), 8.04 (d, J=2.1 Hz, 1H), 7.87 (d, J=8.5 HZ, 1H), 7.76 (dd, J=8.5, 2.1 Hz, 1H), 6.06 (s, 1H), 4.2 (s, 3H), 3.6 (bs, 2H), 2.9 (s, 2H), 2.8 (d, 2H), 1.9 (bs, 2H).

Compound 21
Hydrochloride salt of 8-Chloro-1-(2,4-dichloro-phenyl)-4,5-dihydro-1H-6-thia-1,2-diaza-benzo [e] azulene-3-carboxylic acid piperidin-1-ylamide $^1$HNMR: (DMSO-D$_6$, 300 MHz) δ 10.55 (s, 1H), 7.88 (d, J=2.01 Hz, 1H), 7.80 (d, J=8.50 Hz, 1H), 7.70 (dd, J=10.46, 1.93 Hz, 1H), 7.24 (d, J=1.92 Hz, 1H), 7.05 (dd, J=10.56, 1.93 Hz, 1H), 6.75 (d, J=8.63 Hz, 1H), 4.47 (bs, 1H), 4.23 (bs, 1H), 3.25 (bs, 4H), 3.04 (m, 3H), 1.75 (bs, 4H), 1.40(bs, 2H), 1.18(t, 1H), 1.00(t, 1H).

Compound 22
Hydrochloride salt of 8-Bromo-1-(2,4-dichloro-phenyl)-4,5-dihydro-1H-6-oxa-1,2-diaza-benzo [e] azulene-3-carboxylic acid piperidin-1-ylamide.

$^1$HNMR: (DMSO-D$_6$, 300 MHz) δ 10.52 (s, 1H), 7.86 (d, J=2.01 Hz, 1H), 7.73 (d, J=8.40 Hz, 1H), 7.66 (dd, J=10.43, 1.98 Hz, 1H), 7.30 (d, J=1.99 Hz, 1H), 7.08 (dd, J=10.44, 1.98 Hz, 1H), 6.73 (d, J=8.50 Hz, 1H), 4.48 (bs, 1H), 4.22 (bs, 1H), 3.25 (bs, 4H), 3.08 (m, 3H), 1.77 (bs, 4H), 1.42(bs, 2H), 1.18(t, 1H), 0.99 (t, 1H).

Biological Activity

Compounds of the present invention in the cAMP accumulation model, antagonizes the WIN-55, 212-2 inhibition of forskolin-induced cAMP accumulation in hCB$_1$_CHO cells [J Pharmacol. Exp Ther., 1998, 284, 291-297]. In a mouse vas deferens preparation, representative compounds cause rightward shift of the WIN-55, 212-2 concentration-response curve (Eur. J. Pharm. 1995, 284, 241-247). Representative compounds of the present invention have shown decrease in sucrose solution intake in rat model (Table 1) [Psychopharmacology, 1997, 132, 104-106].

TABLE 1

Effect of representative compounds on the intake of 5% sucrose solution in animal model.

| Compound No. | Reduction in sucrose solution consumption w.r.t. control animals |
|---|---|
| 3 | −18.9 ± 14.0 |
| 5 | −23.2 ± 11.4 |
| 6 | −24.9 ± 8.9 |
| 8 | −30.4 ± 4.3 |
| 16 | −13.2 ± 15.7 |

* formula for calculation:

$$\frac{[\text{Total consumption} - \text{Mean total consumption of control}]}{[\text{Mean total consumption by control}]} \times 100$$

number of animals in a group = 6

No significant adverse effects were observed for any of the mentioned compounds of invention.

We claim:
1. A compound of formula (I):

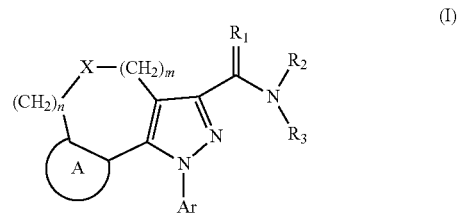

(I)

a tautomeric form, or pharmaceutically acceptable salt thereof, wherein Ar represents a single or fused group selected from the group consisting of aryl, heterocyclyl or heteroaryl group, optionally substituted with one or more groups selected from the group consisting of hydroxy, halo, amino or optionally substituted groups selected from the group consisting of linear or branched alkyl, monosubstituted or disubstituted amino, alkoxy or acyl group wherein the substituted alkyl, monosubstituted or disubstituted amino, alkoxy or acyl group is substituted by one or more of hydroxy, halo, amino, linear or branched alkyl, monosubstituted or disubstituted amino, alkoxy or acyl group;

A represents an optionally substituted phenyl group, X is oxygen or sulfur m is two and n is zero;

wherein when A is substituted, the one or more substituents are the selected from the group consisting of halogen, hydroxyl, thio, nitro, amino, cyano, or an optionally substituted group selected from linear or branched alkyl, alkoxy, thioalkyl, haloalkyl, haloalkoxy, acyl, and aminoalkyl groups; wherein the substituted alkyl, alkoxy, thioalkyl, haloalkyl, haloalkoxy, acyl and aminoalkyl groups are substituted by one or more of halogen, hydroxyl, thio, nitro, amino, cyano, linear or branched alkyl, alkoxy, thioalkyl, haloalkyl, haloalkoxy, acyl, and aminoalkyl groups; and $R_1$ represents O, S, or the group represented by N-Q, where Q represents H or substituted alkyl; or $R_1$ represents the group represented by SO$_2$R", where R" represents H, —OH, halogen or a substituted or unsubstituted group selected from alkyl, aryl, heteroaryl or heterocyclic groups; $R_2$ is either H or (C$_1$-C$_6$) alkyl; $R_3$ is NR$_b$R$_c$ wherein R$_b$ and R$_c$ are the same or different and are selected from an optionally substituted group selected from alkyl, aralkyl or alkenyl or R$_b$ and R$_c$ together with the nitrogen atom to which they are bonded, form a saturated or unsaturated heterocyclic or heteroaromatic radical or a pharmaceutically acceptable salt thereof.

2. The compound as claimed in claim 1, wherein the alkyl group is selected from a linear or branched alkyl group comprising from one to eight carbon atoms.

3. The compound as claimed in claim 1, wherein the aryl group is selected from a monocyclic, bicyclic or tricyclic aryl group.

4. The compound as claimed in claim 1, wherein the aryl group is selected from phenyl, naphthyl, tetrahydronaphthyl, indane, and biphenyl group.

5. The compound as claimed in claim 1, wherein the heterocyclyl is selected from saturated, partially saturated or unsaturated aromatic or non-aromatic mono, bi or tricyclic groups, containing one or more heteroatoms selected from N, O, and S.

6. The compound as claimed in claim 1, wherein the heterocycicyl group is selected from the group consisting of aziridinyl, azetidinyl, pyrrolidinyl, imidazolidinyl, piperidinyl, piperazinyl, 2-oxopiperidinyl, 4-oxopiperidinyl, 2-oxopiperazinyl, 3-oxopiperazinyl, morpholinyl, thiomorpholinyl, 2-oxomorpholinyl, azepinyl, diazepinyl, oxapinyl, thiazepinyl, oxazolidinyl, thiazolidinyl, dihydrothiophene, dihydropyran, dihydrofuran, dihydrothiazole, benzopyranyl, benzopyranonyl, benzodihydrofuranyl, benzodihydrothienyl, pyrazolopyrimidonyl, azaquinazolinoyl, thienopyrimidonyl, quinazolonyl, pyrimidonyl, benzoxazinyl, benzoxazinonyl, benzothiazinyl, benzothiazinonyl, and thieno piperidinyl groups.

7. The compound as claimed in claim 1, wherein the heteroaryl group is selected from optionally fused mono, bi or tricyclic aromatic heteroaromatic groups containing one or more heteroatoms selected from O, N and S.

8. The compound as claimed in claim 1, wherein the heteroaryl group is selected from the group consisting of pyridyl, thienyl, furyl, pyrrolyl, oxazolyl, thiazolyl, isothiazolyl, imidazolyl, isoxazolyl, oxadiazolyl, thiadiazolyl, triazolyl, tetrazolyl, benzofuranyl, benzothienyl, indolinyl, indolyl, azaindolyl, azaindolinyl, pyrazolopyrimidinyl, azaquinazolinyl, pyridofuranyl, pyridothienyl, thienopyrimidyl, quinolinyl, pyrimidinyl, pyrazolyl, quinazolinyl, pyridazinyl, triazinyl, benzimidazolyl, benzotriazolyl, phthalazynil, naphthylidinyl, purinyl, carbazolyl, phenothiazinyl, phenoxazinyl, benzoxazolyl, and benzothiazolyl group.

9. The compound as claimed in claim 1, selected from the group consisting of:
4-Chloro-N-{[8-chloro-1-(2,4-dichloro-phenyl)-1,4,5,6-tetrahydro-1,2-diaza-benzo [e] azulene-3-yl]-methylamino-methylene}-benzenesulfonamide and its pharmaceutically acceptable salts;
8-chloro-1-(2,4-dichloro-phenyl)-4,5-dihydro-1H-6-oxa-1,2-diaza-benzo [e] azulene-3-carboxylic acid piperidin-1-ylamide and its pharmaceutically acceptable salts;
8-chloro-1-(2,4-dichloro-phenyl)-4,5-dihydro-1H-6-oxa-1,2-diaza-benzo [e] azulene-3-carboxylic acid -(4-hydroxy-piperidin-1-yl-amide and its pharmaceutically acceptable salts;
8-chloro-1-(2,4-dichloro-phenyl)-4,5-dihydro-1H-6-oxa-1,2-diaza-benzo [e] azulene-3-carboxylic acid pyrrolidin-1-yl amide and its pharmaceutically acceptable salts;
8-chloro-1-(2,4-dichloro-phenyl)-4,5-dihydro-1H-6-oxa-1,2-diaza-benzo [e] azulene-3-carboxylic acid (hexahydro-cyclopenta[c] pyrrol-2-yl)-amide and its pharmaceutically acceptable salts;
8-chloro-1-(2,4-dichloro-phenyl)-4,5-dihydro-1H-6-oxa-1,2-diaza-benzo [e] azulene-3-carboxylic acid morpholine-4-yl-amide and its pharmaceutically acceptable salts;
8-chloro-1-(2,4-dichloro-phenyl)-4,5-dihydro-1H-6-oxa-1,2-diaza-benz [e] azulene-3-carboxylic acid (4-methyl-piperazine-1-yl)-amide and its pharmaceutically acceptable salts;
8-chloro-1-(4-chloro-phenyl)-4,5-dihydro-1H-6-oxa-1,2-diaza-benzo [e] azulene-3-carboxylic acid piperidin-1-ylamide and its pharmaceutically acceptable salts;
8-chloro-1-(4-chloro-phenyl)-4,5-dihydro-1H-6-oxa-1,2-diaza-benzo [e] azulene-3-carboxylic acid pyrrolidin-1-ylamide and its pharmaceutically acceptable salts;
8-chloro-1-(4-chloro-phenyl)-4,5-dihydro-1H-6-oxa-1,2-diaza-benzo [e] azulene-3-carboxylic acid morpholin-4-ylamide and its pharmaceutically acceptable salts;
7-Chloro-1-(2,4-dichloro-phenyl)-1,5-dihydro-4,6-dithia-1,2-diaza-as-indacene -3-carboxylic acid piperidin-1-ylamide and its pharmaceutically acceptable salts;
7-Chloro-1-(2,4-dichloro-phenyl)-1,5-dihydro-4,6-dithia-1,2-diaza-as-indacene -3-carboxylic acid (hexahydro-cyclopenta [c] pyrrol-2-yl)-amide and its pharmaceutically acceptable salts;
8-Chloro-1-(2,4-dichloro-phenyl)-4,5-dihydro-1H-6-thia-1,2-diaza-benzo [e] azulene-3-carboxylic acid piperidin-1-ylamide and its pharmaceutically acceptable salts; and
8-Bromo-1-(2,4-dichloro-phenyl)-4,5-dihydro-1H-6-oxa-1,2-diaza-benzo [e] azulene-3-carboxylic acid piperidin-1-ylamide and its pharmaceutically acceptable salts.

10. The pharmaceutical composition which comprises a compound as claimed in claim 1 and at least one of a pharmaceutically acceptable carrier, diluent or excipient.

11. The pharmaceutical composition which comprises a compound as claimed in claim 9 and at least one of a pharmaceutically acceptable carrier, diluent or excipient
8-chloro-1-(4-chloro-phenyl)-4,5-dihydro-1H-6-oxa-1,2-diaza-benzo [e] azulene-3-carboxylic acid N'-cyclopropyl-hydrazide and its pharmaceutically acceptable salts;
8-chloro-1-(4-chloro-phenyl)-4,5-dihydro-1H-6-oxa-1,2-diaza-benzo [e] azulene-3-carboxylic acid piperidin-1-ylamide and its pharmaceutically acceptable salts;
1-(2,4-Dichloro-phenyl)-8-methyl-4,5-dihydro-1H-6-oxa-1,2-diaza-benzo [e] azulene-3-carboxylic acid piperidin-1-ylamide and its pharmaceutically acceptable salts;
1-(2,4-Dichloro-phenyl)-8-methyl-4,5-dihydro-1H-6-oxa-1,2-diaza-benzo [e] azulene-3-carboxylic acid pyrrolidin-1-ylamide and its pharmaceutically acceptable salts;
1-(4-chloro-phenyl)-8-methyl-4,5-dihydro-1H-6-oxa-1,2-diaza-benzo [e] azulene-3-carboxylic acid piperidin-1-ylamide and its pharmaceutically acceptable salts;
1-{[8-chloro-1-(2,4-dichloro-phenyl)-1,4,5,6-tetrahydro-7-thia-1,2-diaza -cyclopenta [e] azulene-3-carboxylic acid piperidin-1-ylamide and its pharmaceutically acceptable salts;
8-Chloro-1-(2 4-dichloro-phenyl)-1,4,5,6-tetrahydro-7-thia-1,2-diaza-cyclopenta [e] azulene-3-carboxylic acid (hexahydro-cyclopenta [c] pyrrol-2-yl)-amide and its pharmaceutically acceptable salts;
8-Chloro-1-(2,4-dichloro-phenyl)-4,5-dihydro-1H-6,7-dithia-1,2-diaza-cyclopenta [e]azulene-3-carboxylic acid piperidin-1-ylamide and its pharmaceutically acceptable salts.

12. A process for preparing a compound of formula (I) as claimed in claim 1, wherein Ar, A, X, $R^1$, $R^2$, $R^3$, and m are as defined in claim 1, comprises the steps of:

i) converting a compound of formula (2) to compound of formula (4) by reacting with a substituted hydrazine hydrochloride of formula (3),

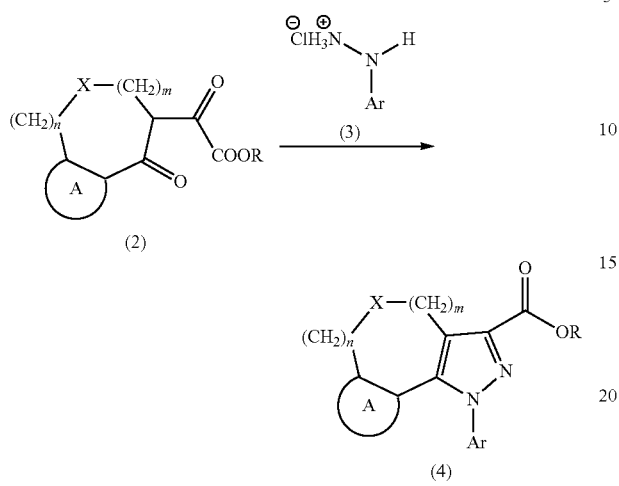

(2)     (3)

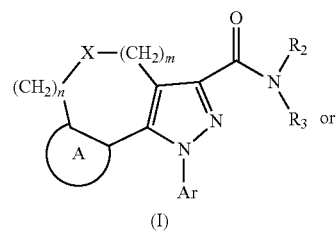

(4)

wherein A, X, m and n are as defined in claim 1 and R is an alkyl group ii) hydrolyzing the compound of formula (4) to obtain the acid of formula (5),

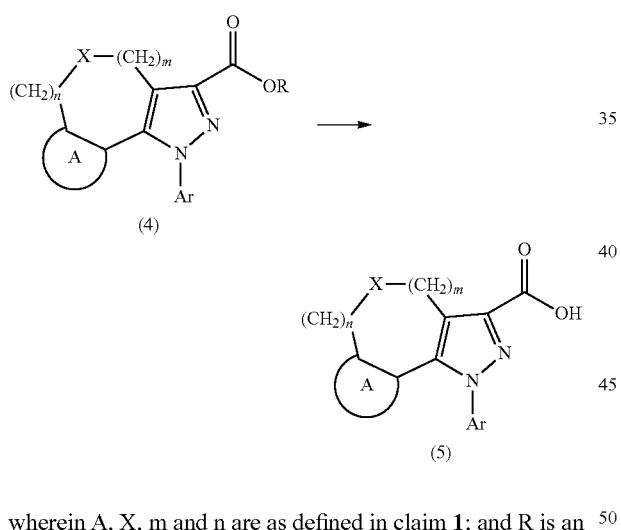

(4)

(5)

wherein A, X, m and n are as defined in claim 1; and R is an alkyl group;

iii) converting the compound of formula (5) to compound of formula (I) by treating with suitable substituted amine of formula $NR_2R_3$, where $R_2$ and $R_3$ are as defined in claim 1,

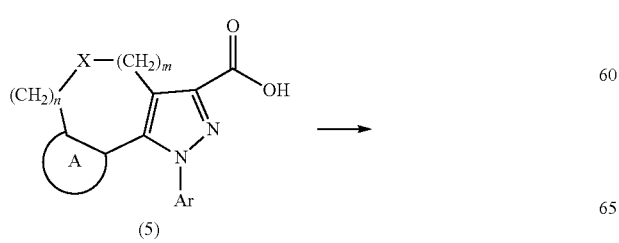

(5)

-continued

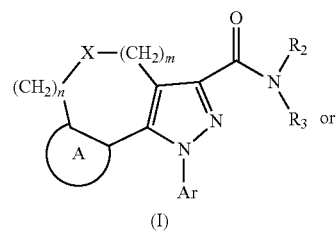

(I)

iv) alternatively, converting the compound of formula (5) to a compound of formula (7) by treatment with a compound of formula $NH_2Q$, where Q is as defined in claim 1,

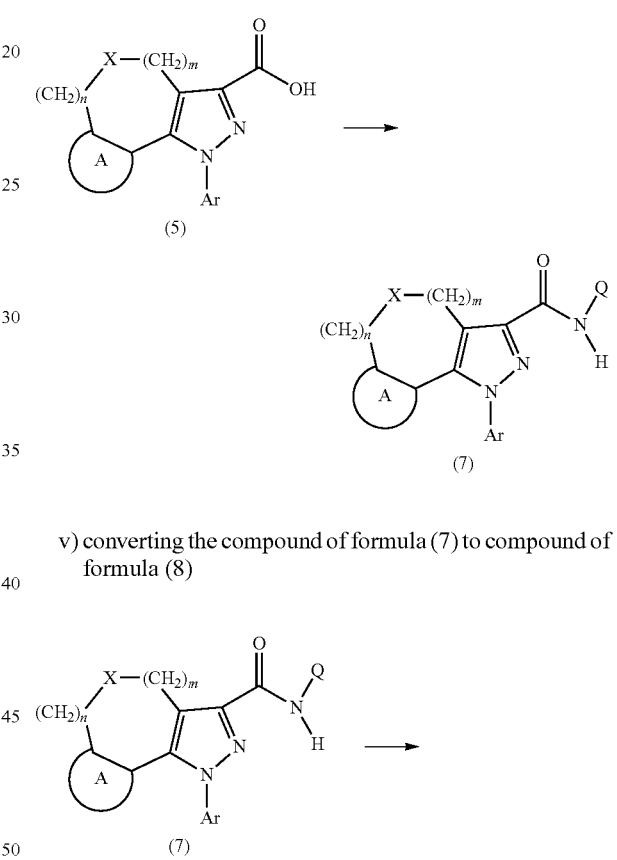

(5)

(7)

v) converting the compound of formula (7) to compound of formula (8)

(7)

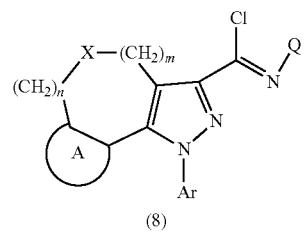

(8)

where Ar, A, X, Q, and m are as defined in claim 1; and vi) converting the compound of formula (8) to a compound of formula (I) by treatment with a substituted amine of formula $NR_2R_3$, where $R_2$ and $R_3$ are as defined in claim 1
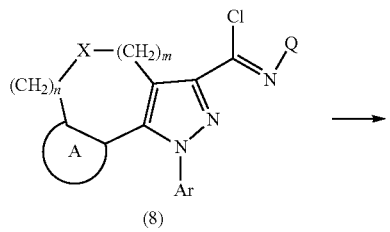
(8)
→
-continued
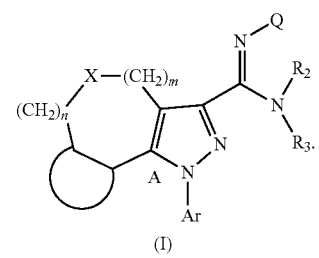
(I)
* * * * *